United States Patent

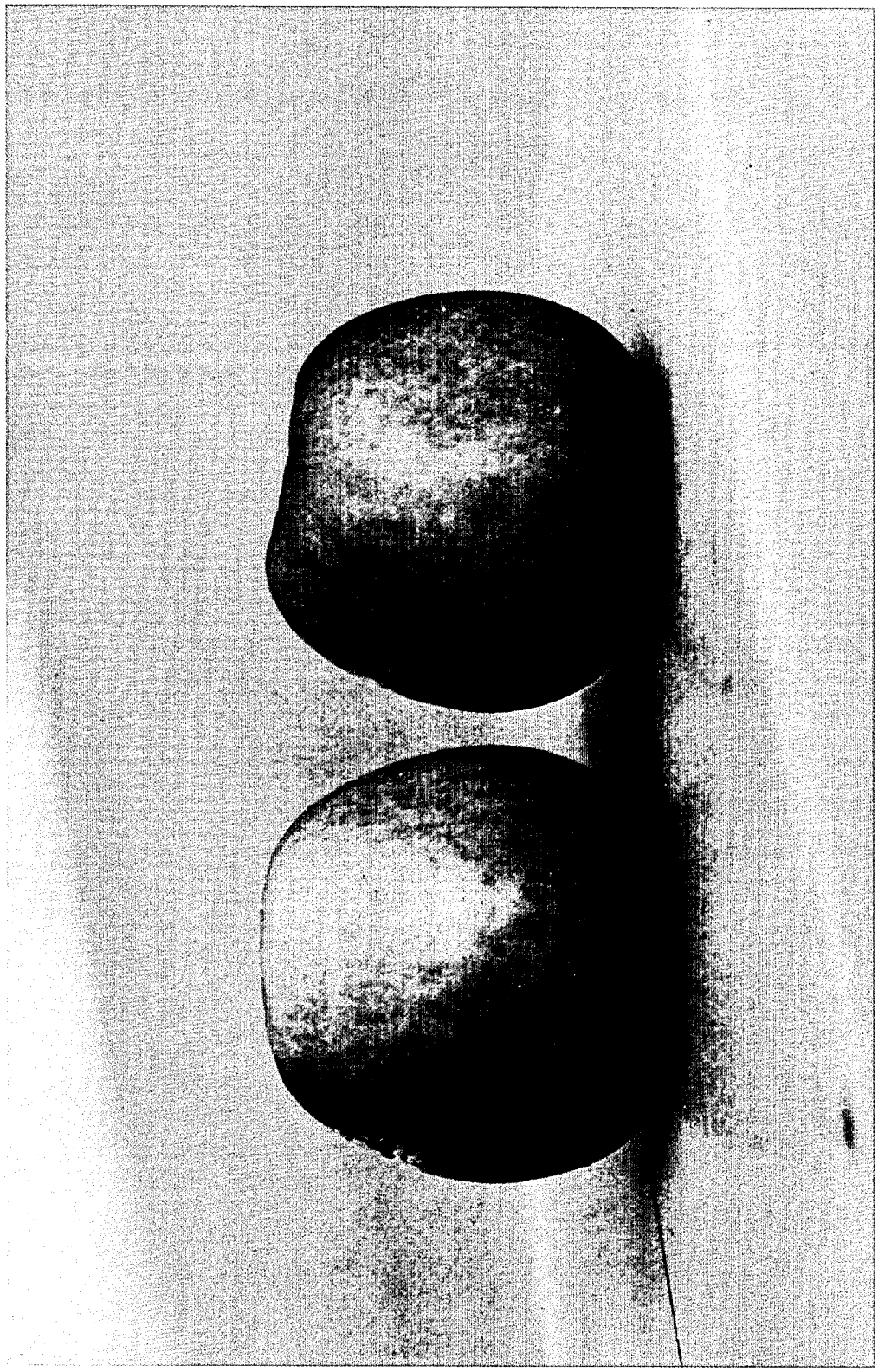

Plant Pat. 3,878
Patented May 4, 1976

3,878
VARIETY OF APPLES

Edwin Saels, 310 Pastorijstraat, 3910 Donk, Herk-de-Stad, Belgium

Filed Oct. 23, 1973, Ser. No. 408,463
Claims priority, application Belgium, Oct. 20, 1972, 790,344
Int. Cl. A01h *5/03*
U.S. Cl. Plt.—34 1 Claim The present invention concerns a new variety of prettily colored, juicy apple, of a delicious taste, preserving very well and especially apt for industrial production.

This new variety of apple, developed by natural mutation, originates from a young wild shoot growing in a row of an orchard of low-stem Golden Delicious trees. The original tree has been well cared for and after some years grafts were grafted on Paradis E.M. type 9 apple trees.

The same care, pruning, watering, quantity of fertilizer, was applied to these young trees as to the Golden Delicious.

The trees obtained are very suitable for massive plantation, Groesbeck system: plus or minus 4,000 trees per hectare. The small trees look like the Golden Delicious but are less spotted on the bark and the color is pinker. They are very productive, have many fruit branches and many buds.

The following are the characteristics:

TREE
- degree of vigor not as strong as the Golden Delicious.
- low standards, height 2 to 2.50 m.
- many fruited branches, leaning downward more than usual.
- many buds on the branches.
- color of leaves: rather dark, and leaves with not very sinuous edges.
- bark little marked, somewhat roseate in color.

FLOWER
- same colors as Golden Delicious.
- smaller than Golden Delicious.
- blooms about 8 days after Golden Delicious, about May 9th.

FRUIT
- conic-oblate axial diameter: about 10 cm., transverse diameter: about 11 cm.
- cavity and stem of Golden Delicious.
- sunken calyx or head.
- very fine skin, changes from salmon-red to the slightly yellowing green of the Golden Delicious.
- flesh is very firm, white, crisp, juicy, bitter-sweet and fresh aromatic taste.
- yields a very good juice.
- table apple, also for very fine compotes.
- stores very well without shriveling.

- good resistance to insects, is almost free of attack by worms and insects.

The apple of this new variety is very similar to the Belle de Boskoop or Reinette with a sunken head. Its lower portion and its tail are similar to the Golden Delicious. Its color presents a very attractive appearance, from the salmon red to slightly yellow green of the Golden Delicious.

Its peel is very fine and, when eating the apple without peeling it, one does not taste the peel.

It is perfect for very fine and very savory sauces. The mealy taste of the Golden Delicious has disappeared.

The apple being very firm, it is invulnerable in transport. It keeps very well under normal refrigeration, at 2 or 3 degrees, until May 15th. On a test basis a part of the crop was placed in a gas cell to entire satisfaction until June 15th.

The apple holds more firmly on the tree than the Golden Delicious and the harvest takes place about two weeks later.

The productivity seems no less than that of the Golden Delicious.

120 young two-year old trees, obtained from the mother tree, have given about 350 kg. of apples.

I claim:

1. A new and distinct variety of apple tree characterized in that the mother tree derives, by natural mutation, from a young shoot growing in a row of low-stem Golden Delicious apple trees and in that grafts from the mother tree have been grafted on Paradis E.M. type 9 apple trees, and further characterized by the following morphological and physiological properties: The tree has the appearance of the Golden Delicious and requires the same care with regard to pruning, watering and fertilizing, is very productive with many fruit branches and buds, and is suitable for massive plantation for industrial production, the apple is conic-oblate, similar to the Belle de Boskoop or Reinette with a sunken head, its lower portion and its tail are those of a Golden Delicious, its very appealing color goes from the salmon red to slightly yellow green of the Golden Delicious, its pulp is very firm, white, crisp and juicy, its peel is very fine, its taste is fresh, aromatic and sour-sweet, it is particularly suitable for making juice of a real apple taste and for making very fine sauces, it withstands transportation very well and keeps under normal refrigeration until May 15th and longer under special conditions.

References Cited

UNITED STATES PATENTS

P.P. 3,308 2/1973 Runkel ---------- Plt.—34

ROBERT E. BAGWILL, Primary Examiner